United States Patent [19]
Pouletty

[11] Patent Number: 5,362,654
[45] Date of Patent: * Nov. 8, 1994

[54] SELF-CONTAINED QUANTITATIVE ASSAY

[75] Inventor: Philippe Pouletty, Atherton, Calif.

[73] Assignee: SangStat Medical Corporation, Menlo Park, Calif.

[*] Notice: The portion of the term of this patent subsequent to Sep. 15, 2009 has been disclaimed.

[21] Appl. No.: 34,604

[22] Filed: Mar. 22, 1993

Related U.S. Application Data

[63] Continuation of Ser. No. 884,373, Jun. 18, 1992, abandoned, which is a continuation of Ser. No. 556,049, Jul. 20, 1984, abandoned, which is a continuation-in-part of Ser. No. 444,814, Dec. 1, 1989, abandoned.

[51] Int. Cl.⁵ ................ G01N 33/543; G01N 33/545
[52] U.S. Cl. ..................... 436/518; 422/58; 422/61; 435/810; 435/975; 436/531; 436/808; 436/810

[58] Field of Search .............. 422/56, 58, 61, 100; 436/810, 975, 531, 518, 808

[56] References Cited

U.S. PATENT DOCUMENTS

| 4,770,853 | 9/1988 | Bernstein ..................... 422/58 |
| 4,842,995 | 6/1989 | Iaccheri et al. ............. 436/810 X |
| 5,147,780 | 9/1992 | Pouletty et al. ............ 422/58 X |

Primary Examiner—Jill A. Johnston
Attorney, Agent, or Firm—Bertram I. Rowland; Bret E. Field

[57] ABSTRACT

Methods and device are provided where a device comprising an absorbing nib, an external deformable container and an internal container having a frangible barrier are provided, where the nib and internal container comprise reagents which are interactive with a sample for measuring an analyte.

11 Claims, 1 Drawing Sheet

SELF-CONTAINED QUANTITATIVE ASSAY

CROSS-REFERENCE TO RELATED APPLICATIONS

This application is a continuation of application Ser. No. 07/884,373, filed Jun. 18, 1992, now abandoned; which is a continuation of application Ser. No. 07/556,049, filed Jul. 20, 1994, now abandoned; which is a continuation-in-part of application Ser. No, 07/444,814, filed Dec. 1, 1989, now abandoned.

INTRODUCTION

1. Technical Field

The field of this invention relates to assay techniques and devices.

2. Background

Many immunoassay procedures have been devised for the purpose of detecting specific analytes. Such assays have found countless applications as tools in medicine. Analyte specific assays have been used to detect antibodies produced in response to infection, components of pathogenic agents, levels of drugs, hormones, and enzymes, etc. In addition to medicine, immunoassays and other related assays have also found numerous applications in manufacturing industries, for example, the detection of food contaminants.

Heterogeneous immunoassays usually involve a ligand or antibody immobilized to a solid support. A sample containing the analyte of interest is passed over the immobilized immunoreagent and the amount of antibody-ligand complex formed is measured. In heterogeneous assays, essential elements include the anchoring of one member of a specific binding pair to a solid support and a means for either directly or indirectly detecting a label bound to the support.

The ease of performing an assay procedure is always an important consideration. Most assays involve the addition of multiple reagents and require multiple washing steps. Ideally, an assay will be simple and not require the use of complex equipment, such as microtiter plate washers or ELISA readers. Immunoassays able to be performed in a physician's office, at home, or in the field are of particular interest and must be developed to be performed without the use of specialized equipment.

There is substantial interest in providing for protocols and devices which are simple, easy to manipulate, and reduce the opportunity for operator failure. The ideal situation would be where an unmeasured sample could be used to provide for a quantitative result and one could avoid any washing or measuring step of the reagents, but could read the result directly.

Relevant Literature

U.S. Pat. Nos. 4,727,19 and 4,632,901 relate to immobilized phase immunoassays devices that produce a colored spot when exposed to a sample containing the appropriate analyte for detection.

SUMMARY OF THE INVENTION

Method and apparatus are provided for performing a non-instrumental assay for the detection of an analyte in a liquid sample. An apparatus is provided that serves as a collector-diluter-dispenser and reaction vessel, comprising a cap-enclosed tube. The apparatus absorbs sample by means of an absorbent nib which comprises a reagent which reacts with the analyte. The apparatus contains a liquid medium restrained from the nib by a frangible barrier which supports the nib, with the nib extending through an opening in the cap. After absorbing the sample with the nib, breaking the barrier drops the nib into the liquid medium and the reacted sample complex may then react with other reagents present in the liquid medium. Exerting pressure on the sides of the apparatus permits the assay medium to be dispensed through the opening originally containing the nib, where the assay medium may be subject to further reaction with development of a signal, which may be read visually or with instrumentation.

DESCRIPTION OF THE SPECIFIC EMBODIMENTS

Figure 1:
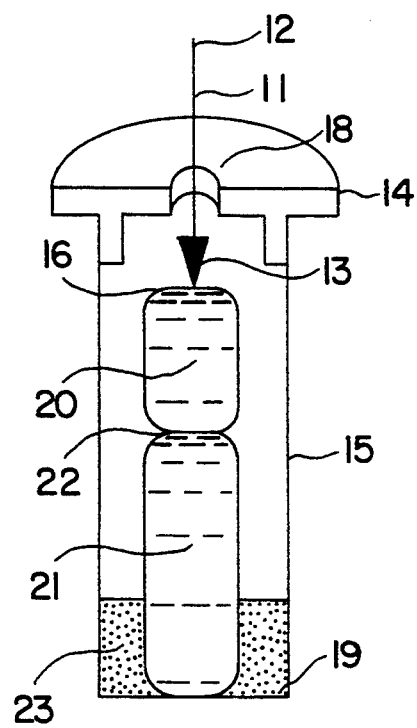
FIG. 1 is an elevational-cross sectional view of the subject apparatus.

Method and apparatus are provided which involve for sequential interaction of a sample with reagents for the determination of a component in the sample. The apparatus comprises a minimum of three essential elements: an external container which is flexible and has an opening; a porous nib which extends through the opening; and a frangible barrier which separates a reagent medium from the nib. The nib has at least one reagent present, which reagent is capable of reacting with the analyte.

The opportunity to have sequential reactions, in a first stage and where the analyte is at an elevated concentration and at a second stage where the analyte has already undergone a first reaction and is now at a diluted stage provides for an enormous flexibility in protocols in detecting a wide variety of analytes. In the first stage, one can provide for rapid reaction between the reagent present in the nib and the analyte in the sample. In the second stage, a somewhat slower reaction is permissible which can be speeded up by providing for relatively high concentrations of the additional reagents. A plurality of containers or ampules can be provided, where dry reagents may also be provided in frangible containers. Depending upon the protocol, one can provide for a signal to be developed in the external container of the apparatus or transfer of all or a portion of the medium to a site where a signal may be developed for detection.

In carrying out the assay, the nib is used to absorb and measure the sample, so that by appropriate control of the size of the nib, one can substantially quantitatively measure a sample volume. The reagent(s) present on the nib may be selected for binding to the analyte for forming a complex, or where one member of a complex is displaced by the analyte or where the analyte becomes bound to the nib, so as to prevent the analyte from becoming dispersed in solution. Each of these approaches may be used in a variety of ways to provide for a detectable signal in proportion to the amount of analyte in the sample.

The analyte may be a ligand or receptor, where the ligand and receptor are defined as members of a specific binding pair which have an affinity for each other of at least about $10^7 M$. The ligand may be a hapten or antigen, where haptens generally range from about 125 to 5000 molecular weight, while antigens generally range from about 2500 molecular weight to any upper limit. Analytes may include naturally occurring ligands and receptors, synthetic compounds, pollutants, contaminants, microorganisms, e.g. viruses, unicellular organisms, etc., blood proteins, surface membrane proteins, cytokines, interferons, hormones, growth factors, etc. Receptors may be naturally occurring or synthetic, for the most part being proteins, such as immunoglobulins, fragments thereof, particularly monovalent fragments, of immunoglobulins, e.g. Fab Fv etc., enzymes, naturally occurring receptors, e.g., T-cell receptors, hormone receptors, surface membrane receptors, lectins, etc. Other specific binding pairs include nucleic acids, e.g. DNA and RNA. For disclosure of specific ligands and receptors, see U.S. Pat. No. 3,996,345, columns 10–17, which disclosure is incorporated herein by reference.

The choice of reagents and protocol will depend to a significant degree upon the sensitivity required for the assay, the manner by which the signal is detected, whether visual or by instrumentation, the degree of quantitation required, the dynamic range of interest, possible interfering components in the sample, the sophistication of the person carrying out the assay, and the like. Thus, the subject device may be used for mixing reagents to provide a specific binding pair complex for use in subsequent stages of an assay, to provide an assay medium to which reagents may be added, to provide a signal which may be measured, or to perform the entire assay, where all the reagents are present in the original device.

Normally, the nib will comprise the complementary member of the specific binding pair to which the analyte is a member. The reciprocal member may be labelled or unlabelled, where the label may be involved directly or indirectly in providing for a detectable signal. As already indicated, an advantage of binding at this stage is that the analyte is at the highest concentration at which it will be in solution during the assay.

The binding entity present in the nib may fulfill a number of functions. It may serve to provide for a much higher number of labels per analyte molecule than a single one step binding might involve. It may provide for binding a first label to the analyte, which might interact with a second label which subsequently becomes bound to the analyte. For example, one may employ fluorescence quenching, where the amount of fluorescence observed in the medium will be substantially reduced by having quencher molecules bound to the analyte. Thus, one could have a complementary specific binding pair member to which fluorescent molecules are conjugated, so that the analyte becomes—decorated with fluorescent label upon being absorbed by the nib.

Another possibility is the presence of an enzyme label which can act in a channeling mode, that is, the product of a first enzyme is the substrate of a second enzyme, where the product of the second enzyme results in a detectable signal. One can provide for protocols and reagents, where the reaction in the absence of binding of the two enzymes to the same molecule is very slow under the conditions of the assay. Therefore, where the product of the second enzyme provides for a detectable signal, the presence of the detectable signal may be attributed to the presence of the analyte. Alternatively, the analyte may serve to release a labelled reagent into solution. FOr example, one could have a specific binding pair complex, where the binding pair member of the complex which is competitive with the analyte is labelled. Thus, in the presence of the analyte, the competitive member will be released into solution. For example, one could have the competitive member labelled with an enzyme, which in subsequent stages would provide for a detectable signal. For example, if the enzyme when bound to an antibody is substantially inhibited from reacting, its release would then provide for an enzyme reaction, which could be observed by means of a detectable product. A third possibility is that the analyte become bound to the porous nib and subsequently acts as a bridge to the binding of a complementary specific binding pair member which is labelled, either directly or indirectly, so that the nib may serve as the source of the detectable signal.

The external container may comprise one or more internal containers, where the internal containers may provide for the sequential combining of different reagents. The reagents may be liquid or solids, e.g. lyophilized. Thus, in the case of an enzyme reaction, one could provide for the sequential addition of enzyme and substrate. For example, in the case of channeling, the analyte would bind to the first enzyme on the nib, bind to the second enzyme in a first solution in a first internal container and then be subjected to the necessary reagents for the channeling reaction, e.g. one or more substrates, buffers, cofactors, etc. Desirably, a scavenger could be included in the assay medium which would destroy the product of the first enzyme which is used as the substrate of the second enzyme. For example, one could use the combination of glucose oxidase and horseradish peroxidase. By employing appropriate dyes, the hydrogen peroxide produced by the glucose oxidase would react with the dyes in solution catalyzed by the horseradish peroxidase. If one included catalase in the assay medium, catalase would scavenge the horseradish peroxidase which was able to escape from the immediate environment of the glucose oxidase and horseradish peroxidase bound to the analyte. In this mode, one would preferentially detect the signal in the external container, carrying out the assay in the container.

Similarly, one could provide for a fluorescent labelled complementary specific binding pair member present in the nib which would bind to the analyte. When the nib was introduced into a first container containing complementary binding pair member conjugated to a quencher, the amount of fluorescence observed would diminish with increasing amounts of analyte. In this case as in all the other cases, there will be times where polyclonal antisera or monoclonal antisera may be preferred. Particularly, where one wishes to have complementary binding pair members binding to an antigen to provide for an interaction, at least one of the antibodies is desirably monoclonal and, where the other is polyclonal, any antibodies competitive with the monoclonal antibody have been removed.

Where the analyte binds to the nib, one could provide for a "sandwich" assay where the analyte serves as a bridge for the binding of labelled specific binding pair member to the nib. Where the label is a fluorescer, it may be sufficient to remove the nib from the container, wash the nib, and measure its fluorescence. Alternatively, where the label is an enzyme, this may require a second container containing the substrate for the enzyme, where the substrate produces a fluorescent product or a readily observable dye. Thus, one would break the barrier to the first container, the nib would become immersed in the enzyme conjugate, and the enzyme conjugate would bind to the nib in accordance with the amount of analyte present. One could then break a second barrier or container, and by providing for an insoluble product, which would not adsorb to the nib, any product formed on the nib would precipitate on the nib and remain, while product produced in solution would precipitate to the floor of the container. One could remove the nib from the medium and by determining the amount of colored dye or fluorescer present on the nib, determine the amount of analyte in the sample medium.

Numerous other protocols may also be used, which do not require the transfer of the assay medium to another site.

Alternatively, one may use the subject apparatus for preparing the assay medium for transfer to another site. Thus, the intent will normally be to provide for the individual incubations during the contact with the nib, followed by the contact with other reagents either in a single step, or sequentially in a number of steps. Once the various incubations have been carried out, one may then transfer the medium in whole or in part to a membrane, bibulous member, capillary, or the like, for any further manipulations to be carried out. Manipulations may include washing to remove non-specifically bound complexes, application of developer agents, binding of the complex by complexation between specific binding pair members, adsorption, etc. Since there will have already been the incubation between the sample and some of the reagents, very rapid reactions may now be carried out for the assay.

An exemplary assay would allow for substantial multiplication of the number of labels to an analyte. For example, one could employ an antigen, where the nib comprised biotin labelled monoclonal antibody to the antigen, and the analyte would bind to the biotin-conjugated antibody. The internal container would comprise streptavidin conjugated enzyme. Thus, upon breaking the barrier which allows the nib to become immersed in the medium, the analyte-(biotin-conjugated antibody) complex would bind to the enzyme conjugated streptavidin. One could then transfer a portion of the assay medium, conveniently through the opening through which the nib extended as one or more drops onto a membrane to which a monoclonal antibody different from the first monoclonal antibody is bound, which antibody recognizes a different epitopic site of the analyte from the first antibody. The analyte complex would bind to the membrane surface and any non-specific enzyme could be washed away by following the addition of the assay medium with a convenient wash solution, e.g. phosphate buffered saline. One could then add developer solution to the site to which the assay medium had been added and determine the color.

In one aspect, disclosed in co-pending application Ser. No. 444,814 filed on Dec. 1, 1989 the antibody is added so as to provide for a highly concentrated internal circle of antibody surrounded by a concentric circle of antibody at a substantially lower concentration. In this situation, where the analyte is present below a predetermined level, it will be substantially concentrated in the internal circle. When it exceeds a certain concentration, it will expand into the external circle. Thus, upon adding developer solution, where the analyte is present below a predetermined concentration, a dark central colored region will occur, while if it exceeds the predetermined concentration, there will be a dark central color surrounded by a lighter colored region.

Turning now to a consideration of the apparatus, the nib may be any convenient sample, particularly water, insoluble porous material, normally a hydrophilic material, and may be of any convenient dimension or configuration. In addition, the nib may be fitted with a lancet for a finger prick to obtain a blood sample. The shape of the nib could be modified to allow for a swab collection from urethra, for example, a nib in the shape of a threaded screw. Various reagents may be bound to the nib, either by absorption or covalent bonding. The nib may be dry as a result of vacuum drying, heating, evaporation, lyophilization, or damp, where the nib may be maintained in a covered state to prevent evaporation and allow for a wet environment. The wet environment may also be achieved by using various high boiling hydroxylic compounds, such as glycerol, mannitol, diethyleneoxy alcohol, etc. Where proteins are bound to the nib, it may be desirable to provide for various stabilizers, such as sugars, the hydroxylic compounds indicated above, biocides, etc.

Figure 2:
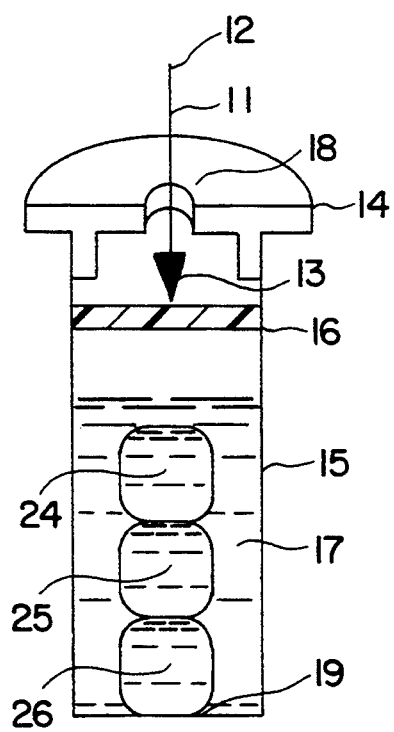
FIG. 2 is an elevational-cross sectional view of an alternate embodiment of the subject apparatus.

A collector-diluter-dispenser apparatus is depicted in FIGS. 1 and 2. The collector-diluter-dispenser apparatus comprises the following structural components: a hydrophilic nib 11, a cap 14 for retaining the nib from falling out of the collector-diluter-dispenser apparatus, a flexible tubular container 15, enclosed by cap 14, and a frangible barrier 16 restraining the flow of the liquid medium and supporting the nib from falling into the liquid medium, while the nib 11 extends through an aperture 18 in the cap 14.

The device provides for a plurality of reagents. In FIG. 1, frangible vials 20 and 21 are stacked at interfare 22, each vial containing the same or different reagent medium.

Powder 23 is at the bottom of the frangible container 15, so that a total of three different reagents are provided, where all three may be mixed simultaneously, or the liquid vials may be mixed sequentially, breaking one vial to dissolve the powder 23 while the nib 11 is immersed in the mixture, followed by breaking the other vial and releasing the fluid in the vial to mix the assay mixture.

In FIG. 2, three frangible vials 24, 25 and 26 are stacked one upon the other in medium 12. The three vials may be broken independently, sequentially, or simultaneously, while the nib is immersed in medium 17, or prior to immersion. Thus, interactive reagents may be stored together and released as appropriate, prior to, simultaneously with, or subsequent to immersion of the nib in the medium 13.

The use of the collector-diluter-dispenser is described as follows. Liquid sample is contacted with the nib 11 of the collector-diluter-dispenser. Once the sample has been absorbed by the nib, the nib is withdrawn from the sample source, and the nib end of the collector-diluter-dispenser is pointed upwards. The frangible barrier 16 within the device is broken, and the breaking of the barrier 16 allows the sample containing nib 11 to fall into the liquid medium 17 where the sample is released from the nib 11 and dispensed into the frangible container. The nib is capable of absorbing molecules, particles, e.g., virus particles, cells, etc., and effectively dispersing them into a liquid medium. As indicated above, by using a plurality of vials, one can bring together a number of reagents during the assay determination, which can be safely stored together in the subject device. After the assay medium and sample have mixed, thus diluting the sample, the collector-diluter-dispenser may be used as a dropper to dispense the diluted sample. The collector-diluter-dispenser may be used as a dropper because the main tube 15 is made from a flexible material that deforms under pressure, and diluted sample is free to flow through an aperture 18 in the cap through which the nib 11 had previously extended.

After the liquid medium and sample have mixed, thus diluting the sample, the medium may now be mixed with additional media present in the external container by breaking additional frangible barriers or the apparatus may be used as a dropper to dispense the assay medium for the next stage of the assay. The subject apparatus may be used as a dropper because the external container 15 is made from a flexible material that deforms under pressure and the assay medium is allowed to flow through the aperture 18 in the cap, through which the nib 11 had previously extended.

The nib 11 serves several functions. The nib is able to absorb sample and also release, when appropriate, the absorbed sample into the liquid medium 17. The nib also has a measuring function. Essentially identical nibs will be able to take up and release reproducible quantities of sample, so that pre-determined dilution ratios may be reproducibly attained.

The nib 11 also serves an active role by providing for various reagents for reaction with the analyte. In addition, the nib may also include in dehydrated form, anticoagulants (EDTA, citrate, heparin), detergents, etc.

Once the nib 11 has been used to collect the sample, the sample may be allowed to dry on the nib 11 or allowed to be dipped into other liquid for washing or other reactor, prior to release of the sample into the liquid medium or the sample containing nib may be mixed with the liquid medium before substantial drying takes place.

The nib 11 will usually be composed of a hydrophilic relatively deformable resistant material that will be substantially inert to the analyte of interest and the sample. The nib is made of a hydrophilic material so that an aqueous sample will be drawn up the nib when the nib is touched to a fluid sample. Exemplary, but not exclusive of materials suitable for the nib are nylon, polyethylene, or polypropylene. Preferably, the nib material is nylon, more preferably the nibs are N99356 produced by American Filtrona.

Conveniently, the nib may be essentially cylindrically shaped with the exposed end of the nib being pointed. The pointed end 12 of the nib may be contacted with the sample to be analyzed. As already indicated, other forms may find specific use, depending upon the nature of the sample. The opposing end of the nib has a bulbous shape 13 having a diameter somewhat larger than the diameter of the aperture 18 of the cap 14. The cylindrical nib will usually have a length of about 3 mm to 4 cm and a diameter of about 0.2 to 3 mm, depending upon the sample size to be employed.

The cap 14 is mounted onto a flexible tube 15 sealed at one end 19. The flexible tube is made of a material that readily deforms under squeezing. Exemplary of materials for the tube are plastics such as polyethylene, polypropylene or other inert elastomeric materials. The precise dimensions of the tube are not critical, the tube conveniently having a volume of from about 1 to 10 ml, more usually form about 1 to 5 ml.

The barrier 16 as well as vials 20, 21 and 24–26, are made of a frangible material, particularly glass or plastic, and are of a thickness such that they are easily broken under hand pressure. The material should be inert to both the liquid medium and the sample. There are many possible configurations of the barrier 16 that permit it to both support the nib and restrict the flow of the liquid medium. Two possible configurations are given in FIGS. 1 and 2. In FIG. 1, the barrier 16 is the top of an ampule containing the liquid medium. In FIG. 2, the barrier 16 is a disk extending completely across the flexible tube.

The composition of the liquid medium 17 will vary in accordance with the requirements of specific assays. In general, the liquid medium will be an aqueous solution. The liquid medium 17 will also contain compounds that have functions in the assay other than serving to dilute the sample. For example, the liquid medium may contain buffers and/or non-specific binding blocking agents, e.g., bovine serum albumin, casein, serum, etc. The compositions in the other vials may be various agents, with as specific binding pair members, enzyme inhibitions, complexing agents, oxidizing or reducing agents, enzyme cofactors, or the like.

In carrying out the assay, one would contact the nib with the sample in accordance with the nature of the sample. Once the nib had become saturated with the sample, it would then be removed form the sample and allowed to incubate in accordance with the assay. After sufficient time for incubation, the frangible barrier is broken and the nib allowed to become immersed in the liquid medium. Some agitation may be employed for sufficient time for any reactions to occur and, as appropriate, dispersion of the analyte or analyte complex into the liquid medium. After sufficient time for incubation, usually not exceeding about 30 min, a reading may be taken or the apparatus used to dispense one or more drops of the medium to the next stage of the assay.

The following examples are offered by way of illustration and not by way of limitation.

EXPERIMENTAL

The apparatus employed is sold as a Dipette ™, comprising a nylon nib (NIB99356) having a length of 27.7 mm, a diameter of 1.9 mm, and a total volume of 78.5$^3$ mm for absorption of a volume of liquid=50 mm3. The lower end of the nib contains in a freeze-dried form a goat anti-human albumin biotin conjugate antibody (2.5 $\mu$l of a 0.5 mg/ml solution from American Qualex). The external container has a volume of 5 ml and encloses a glass ampule containing 1.2 ml of alkaline phosphatase/streptavidin conjugate diluted to 5 $\mu$g/ml in 0.1M carbonate/bicarbonate, pH 9.6, with 1% casein and 0.05% sodium azide.

The device is used to collect a volume of a urine specimen, whereby any albumin in the specimen reacts with the goat anti-human albumin-biotin conjugate antibody. The external tube is then squeezed to break the glass ampule. The nib falls into the alkaline phosphatase/streptavidin conjugate solution, and the mixture is agitated for about 30 sec. During this time, the albumin/goat anti-human albumin biotin conjugate antibody complex is released form the nib into the alkaline phosphatase/streptavidin conjugate solution to provide for binding of the alkaline phosphatase to the albumin. The apparatus is then used to dispense six drops of the medium to a capped Stat test cartridge.

The test cartridge is described in the parent application and is available from Sangstat as STAT cartridge.

After adding the three drops of the medium, the site is washed with a wash solution (0.05M borate pH 8 with 0.01% thimerosal w/v). Approximately 1 ml of the wash solution is used and allowed to drain completely. The wash solution is followed by adding 200 $\mu$l of a chromogenic substrate (bromochloroindoxyl phosphate solution). After waiting three minutes, the result may be read. Alternatively, the result may be read again five to ten minutes later, adding 200 µl of a stopping solution 0.2M phosphate pH 6 to the assay site.

It is evident from the above description, that the subject device provides for extreme convenience in allowing for the simple mixing of reagents without requiring careful measuring. The reagents may be stored in stable form for long periods of time and the reaction is allowed to proceed in a convenient container. In addition, reactions can be allowed to occur prior to any dilution of the sample as used so that smaller amounts of a reagent may be employed while assuring complete reaction of the analyte. Thus, the subject device provides for the convenient preparation of an assay medium, where the result may be directly read in the device or the assay medium transferred in whole or part to a different device for subsequent determination.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A collector-diluter-dispenser device useful for processing a sample for a diagnostic assay and quantitatively measuring a sample volume, said device comprising:
   a compressible tube enclosed at one end;
   a cover mounted over the open end of said tube and comprising at least one aperture;
   a liquid medium in said tube;
   a first frangible barrier separating said medium from said aperture;
   at least one absorbent nib in said tube and extending through said aperture, said nib comprising means for preventing said nib to pass through said aperture, providing substantially quantitative release of said sample into said liquid medium for allowing for quantitative determination of an analyte in said sample; and
   a second frangible barrier supporting said nib to maintain said nib extending through said aperture, wherein said first and second frangible barriers may be the same.

2. A device according to claim 1, wherein said first frangible barrier is a sealed frangible container enclosing said medium.

3. A device according to claim 1, wherein said frangible barrier is a disk extending across said tube.

4. A device according to claim 1, wherein said nib has a pointed end.

5. A device according to claim 1, wherein said nib is impregnated with at least one reagent.

6. A device according to claim 1, wherein said tube has a plurality of media or powders separated from each other by frangible barriers.

7. A collector-diluter-dispenser device useful for processing a sample for a diagnostic assay and quantitatively measuring a sample volume, said device comprising:
   a compressible tube enclosed at one end;
   a cover mounted over the open end of said tube and comprising at least one aperture;
   a liquid medium in said tube;
   a first frangible barrier separating said medium from said aperture;
   at least one absorbent nib in said tube and extending through said aperture, said nib comprising means for preventing said nib to pass through said aperture and impregnated with at least one reagent useful in the determination of an analyte, providing substantially quantitative release of said sample into said liquid medium for allowing for quantitative determination of an analyte in said sample; and
   a second frangible barrier supporting said nib to maintain said nib extending through said aperture, wherein said first and second frangible barriers may be the same.

8. A device according to claim 7, wherein said reagent is the complementary member of a specific binding pair, wherein said analyte is the other member of said specific binding pair.

9. A device according to claim 8, wherein said complementary member is conjugated to a label capable of providing a detectable signal.

10. A device according to claim 8, wherein said compressible tube comprises at least one container in said tube comprising a frangible barrier.

11. A device according to claim 7, wherein said compressible tube comprises at least one container in said tube comprising a frangible barrier.

* * * * *